(12) United States Patent
Sell et al.

(10) Patent No.: US 10,022,104 B2
(45) Date of Patent: Jul. 17, 2018

(54) MARKERS, PHANTOMS AND ASSOCIATED METHODS FOR CALIBRATING IMAGING SYSTEMS

(71) Applicant: ELEKTA AB (PUBL), Stockholm (SE)

(72) Inventors: Martin Sell, Horley (GB); David Mills, Edenbridge (GB); Julian Byrne, West Sussex (GB); John Allen, West Sussex (GB); David Anthony Roberts, East Grinstead (GB)

(73) Assignee: ELEKTA AB (PUBL), Stockholm (SE)

( * ) Notice: Subject to any disclaimer, the term of this patent is extended or adjusted under 35 U.S.C. 154(b) by 126 days.

(21) Appl. No.: 14/781,019

(22) PCT Filed: Mar. 28, 2014

(86) PCT No.: PCT/EP2014/056272
§ 371 (c)(1),
(2) Date: Sep. 28, 2015

(87) PCT Pub. No.: WO2014/154861
PCT Pub. Date: Oct. 2, 2014

(65) Prior Publication Data
US 2016/0038116 A1 Feb. 11, 2016

(30) Foreign Application Priority Data

Mar. 28, 2013 (GB) .................................. 1305751.8
Oct. 28, 2013 (GB) .................................. 1318959.2

(51) Int. Cl.
*A61B 6/00* (2006.01)
*A61B 6/03* (2006.01)
(Continued)

(52) U.S. Cl.
CPC .............. *A61B 6/584* (2013.01); *A61B 6/582* (2013.01); *A61B 6/583* (2013.01); *A61B 90/39* (2016.02);
(Continued)

(58) Field of Classification Search
CPC ......... A61B 6/583; A61B 6/582; A61B 6/584; A61N 5/1075; A61N 2005/1076; G01R 33/4808; G01R 33/4812
(Continued)

(56) References Cited

U.S. PATENT DOCUMENTS 4,945,914 A * 8/1990 Allen ....................... A61B 6/12
600/426
5,368,030 A * 11/1994 Zinreich .................. A61B 6/12
324/309

(Continued)

FOREIGN PATENT DOCUMENTS

GB        2182450 A      5/1987
GB        2212371 A      7/1989
(Continued)

OTHER PUBLICATIONS

International Search Report in PCT/EP2014/056272, dated Aug. 1, 2014.
(Continued)

*Primary Examiner* — Allen C. Ho
(74) *Attorney, Agent, or Firm* — Finnegan, Henderson, Farabow, Garrett & Dunner LLP

(57) ABSTRACT

Embodiments of the present invention provide markers, phantoms, and associated methods of calibration which are suitable for use in both magnetic resonance imaging and radiographic imaging systems. A marker includes a first marker component having a first hydrogen proton density and a first mass density; and a second marker component (Continued)

having a second hydrogen proton density different than the first hydrogen proton density, and a second mass density different than the first mass density. The first marker component and the second marker component are non-magnetic.

17 Claims, 5 Drawing Sheets

(51) Int. Cl.
    *A61N 5/10*     (2006.01)
    *G01R 33/48*     (2006.01)
    *G01R 33/58*     (2006.01)
    *A61B 17/00*     (2006.01)
    *A61B 90/00*     (2016.01)

(52) U.S. Cl.
    CPC ....... *A61N 5/1075* (2013.01); *G01R 33/4808* (2013.01); *G01R 33/4812* (2013.01); *G01R 33/58* (2013.01); *A61B 2017/00707* (2013.01); *A61B 2017/00725* (2013.01); *A61B 2090/3954* (2016.02); *A61B 2090/3966* (2016.02); *A61B 2090/3995* (2016.02); *A61N 2005/1076* (2013.01)

(58) Field of Classification Search
    USPC .................................................. 378/207, 65
    See application file for complete search history.

(56) References Cited

U.S. PATENT DOCUMENTS

| | | | | |
|---|---|---|---|---|
| 5,442,674 | A * | 8/1995 | Picard | A61B 6/583 |
| | | | | 378/18 |
| 5,469,847 | A | 11/1995 | Zinreich et al. | |
| 6,044,132 | A * | 3/2000 | Navab | A61B 6/4441 |
| | | | | 378/163 |
| 6,333,971 | B2 * | 12/2001 | McCrory | A61K 49/0409 |
| | | | | 378/162 |
| 6,687,533 | B1 | 2/2004 | Hirano et al. | |
| 6,851,855 | B2 * | 2/2005 | Mitschke | A61B 6/547 |
| | | | | 378/205 |
| 6,965,235 | B1 | 11/2005 | Guclu et al. | |
| 7,010,095 | B2 * | 3/2006 | Mitschke | A61B 90/36 |
| | | | | 378/162 |
| 7,016,456 | B2 * | 3/2006 | Basu | A61B 6/032 |
| | | | | 378/18 |
| 7,147,373 | B2 * | 12/2006 | Cho | A61B 6/547 |
| | | | | 378/164 |
| 7,413,573 | B2 * | 8/2008 | Hartley | A61F 2/07 |
| | | | | 623/1.13 |
| 7,697,738 | B2 * | 4/2010 | Da Silva | A61B 6/12 |
| | | | | 382/128 |
| 7,702,378 | B2 * | 4/2010 | Bolan | A61B 19/54 |
| | | | | 600/414 |
| 7,925,326 | B2 | 4/2011 | Siegel et al. | |
| 7,950,849 | B2 * | 5/2011 | Claus | A61B 6/583 |
| | | | | 378/18 |
| 8,007,173 | B2 * | 8/2011 | Paidi | A61B 6/584 |
| | | | | 378/207 |
| 8,043,003 | B2 * | 10/2011 | Vogt | G01N 23/046 |
| | | | | 378/207 |
| 8,104,958 | B2 * | 1/2012 | Weiser | A61B 6/583 |
| | | | | 378/162 |
| 8,180,130 | B2 * | 5/2012 | Sebok | G06T 7/74 |
| | | | | 378/20 |
| 8,186,880 | B1 | 5/2012 | Arnold | |
| 8,220,994 | B2 * | 7/2012 | Heigl | A61B 6/547 |
| | | | | 378/207 |
| 8,244,330 | B2 * | 8/2012 | Meier | A61N 5/1049 |
| | | | | 600/407 |
| 8,363,919 | B2 * | 1/2013 | Sebok | G06K 9/3216 |
| | | | | 378/4 |
| 8,380,288 | B2 * | 2/2013 | Labadie | A61B 5/06 |
| | | | | 600/407 |
| 8,544,162 | B2 * | 10/2013 | Bolan | A61B 19/54 |
| | | | | 29/460 |
| 8,588,888 | B2 * | 11/2013 | Ma | A61B 5/0035 |
| | | | | 600/411 |
| 8,666,133 | B2 * | 3/2014 | Vermandel | G01N 29/0654 |
| | | | | 378/207 |
| 8,721,660 | B2 * | 5/2014 | Ulfarsson | A61B 5/055 |
| | | | | 600/426 |
| 8,728,081 | B2 * | 5/2014 | Lauchner | A61B 17/8855 |
| | | | | 604/101.05 |
| 8,771,290 | B2 * | 7/2014 | Mitchell | A61B 90/11 |
| | | | | 248/181.1 |
| 8,798,716 | B1 * | 8/2014 | DeSena | A61B 19/54 |
| | | | | 600/3 |
| 8,821,364 | B2 * | 9/2014 | Fisher | A61K 9/0024 |
| | | | | 424/1.25 |
| 9,014,787 | B2 * | 4/2015 | Stubbs | A61N 5/1049 |
| | | | | 600/426 |
| 9,042,958 | B2 * | 5/2015 | Karmarkar | A61B 5/0476 |
| | | | | 600/411 |
| 9,082,036 | B2 * | 7/2015 | Sebok | G06K 9/3216 |
| 9,082,177 | B2 * | 7/2015 | Sebok | G06T 7/0028 |
| 9,123,096 | B2 * | 9/2015 | Miyasa | G06T 7/0012 |
| 9,265,590 | B2 * | 2/2016 | Zagorchev | A61B 6/508 |
| 9,459,333 | B2 * | 10/2016 | Bao | G01R 33/481 |
| 9,463,074 | B2 * | 10/2016 | Gibson | A61B 90/39 |
| 9,579,077 | B2 * | 2/2017 | Casanova | A61B 6/481 |
| 9,726,745 | B2 * | 8/2017 | Bourne | A61N 5/1075 |
| 2001/0004395 | A1 | 6/2001 | McCrory et al. | |
| 2006/0293581 | A1 * | 12/2006 | Plewes | A61B 5/055 |
| | | | | 600/407 |
| 2011/0105896 | A1 | 5/2011 | Zagorchev et al. | |
| 2012/0179025 | A1 | 7/2012 | Ma et al. | |
| 2013/0267829 | A1 * | 10/2013 | Ojha | A61B 6/032 |
| | | | | 600/411 |

FOREIGN PATENT DOCUMENTS

| | | |
|---|---|---|
| WO | WO 2006/119645 A1 | 11/2006 |
| WO | WO 2012/080973 A2 | 6/2012 |
| WO | WO 2013/144802 A1 | 10/2013 |

OTHER PUBLICATIONS

UK Intellectual Property Office Search Report in GB1305751.8, dated Oct. 25, 2013.
UK Intellectual Property Office Search Report in GB1318959.2, dated Mar. 19, 2014.

* cited by examiner

MARKERS, PHANTOMS AND ASSOCIATED METHODS FOR CALIBRATING IMAGING SYSTEMS

CROSS-REFERENCE TO RELATED PATENT APPLICATIONS

This application is a National Stage Entry of International Application No. PCT/EP2014/056272, filed Mar. 28, 2014, which claims priority from Great Britain Application No. 1318959.2, filed Oct. 28, 2013, and Great Britain Application No. 1305751.8, filed Mar. 28, 2013. The entire contents of the above-referenced applications are expressly incorporated herein by reference.

TECHNICAL FIELD

The present invention relates to medical imaging, and particularly to markers, phantoms, and associated methods of calibrating an imaging system which may be integrated with a radiotherapy system.

BACKGROUND

Recent developments in the field of radiotherapy have focussed on integrating an imaging system with the therapeutic system. The goal is to provide real-time feedback on the location of an anatomical feature within the patient (e.g. a tumour) such that a therapeutic radiation beam can be more accurately controlled to target that feature.

One suggested approach is to combine a linear accelerator-based therapeutic system with a magnetic resonance imaging (MRI) system within a single apparatus, known as an MRI-Linac. Such apparatus is described in a number of earlier applications by the present Applicant, including U.S. patent application Ser. No. 12/704,944 (publication no 2011/0201918) and PCT publication no 2011/127947. In the system described in each of these earlier applications, the magnetic coils of the MRI system are split, leaving a gap through which a therapeutic radiation beam can be delivered to the patient. In this way, the patient can be imaged and treated substantially simultaneously while lying in the same position.

If the MRI system is to provide reliable information to the therapeutic system, it is important that the two systems are accurately calibrated; that is, the coordinate system of the MRI system must be registered to that of the treatment beam so that measurements in the MRI system can be translated into instructions in the therapy system.

Phantoms are known devices which are scanned or imaged to evaluate and tune the performance of various medical imaging devices. A paper by Rhode et al ("Registration and Tracking to Integrate X-Ray and MR Images in an XMR Facility", IEEE Transactions on Medical Imaging, Vol. 22, pages 1369-1378) describes a method of registering x-ray and MR images in which a phantom is first imaged in an x-ray system before being translated a distance and imaged by an MRI system. The distance between the two systems is measured to enable the two coordinate systems to be co-registered. When in the x-ray system, ball bearings are used as markers within the phantom; when in the MRI system, the ball bearings are replaced by MR imaging markers to avoid problems arising from interactions with the intense magnetic field.

This system has several drawbacks. The replacement of the ball bearings with MR imaging markers introduces a potential source of error if the two markers are not exactly co-located within the phantom. In addition, the translation of the phantom between the two devices introduces a further source of error.

SUMMARY OF INVENTION

According to a first aspect of the present invention, there is provided a marker for use in calibration of a medical imaging system, comprising: a first component having a first hydrogen proton density and a first mass density; and a second component having a second hydrogen proton density different than the first hydrogen proton density, and a second mass density different than the first mass density, wherein the first and second components are non-magnetic.

In further aspects of the invention, phantoms and methods of calibrating imaging systems are provided.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

Figure 1:
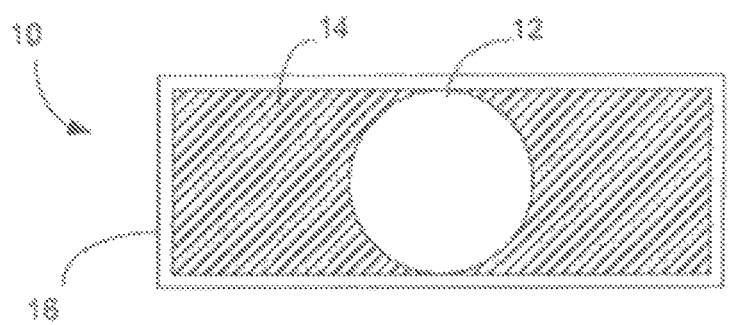
FIG. 1 shows a marker according to embodiments of the present invention.

FIG. 1 shows a cross section of a marker 10 according to embodiments of the present invention. As will be explained below, the marker 10 is suitable for use in a variety of medical imaging systems using different imaging modalities.

In order to understand how the marker 10 works, it is instructive first to consider the different imaging mechanisms which may be employed in medical imaging.

Magnetic resonance imaging (MRI) operates by placing the imaging object in a high strength magnetic field. Currently, the field strength density typically varies from system to system between 0.2 and 3 T. In this strong magnetic field, the magnetic moments of hydrogen protons in the object become aligned with the magnetic field. By applying an electromagnetic signal having a resonant frequency to the object, the spins of those protons can be made to flip. When the electromagnetic signal is switched off, the protons flip back and emit an electromagnetic signal which can be received in receiver coils. Gradient magnets are employed to vary the magnetic field spatially, so as to generate detectable signals only from certain locations within the object and/or to make the resonant frequency differ at different locations to enable spatial encoding of received electromagnetic signals. Hydrogen protons in different materials return to their equilibrium state at different relaxation rates, and this can also be used to differentiate between materials and construct images.

In this way, materials with high hydrogen proton densities, i.e. materials with high numbers of hydrogen protons which are free to flip their magnetic moment, are clearly and strongly visible in MR images.

Another imaging modality employs radiation such as x-rays. An object to be imaged is targeted with a collimated x-ray beam; typically the beam is cone-shaped, but other shapes could be employed. A detector positioned on the opposite side of the body detects the radiation after it has passed through the object. Some of the radiation will have been absorbed by the object, such that the data collected by the detector provides information on the location of the object in the form of a projection image. This technique is known in the art and termed herein as radiography. Multiple projection images can be combined to reconstruct a volume image of the object using computed tomography (CT) techniques. Note, positron emission tomography (PET) employs electromagnetic radiation in the form of gamma rays, but is not a radiographic technique.

The likelihood of an object absorbing x-rays of a given energy increases with increasing material density of the object, although the increase is not linear. High-density materials such as lead or tungsten absorb x-rays very readily, which leads to them being employed in collimators, radiation shields and the like. Low-density objects may not be visible in radiation-based images. The likelihood of absorption also depends on the energy of the radiation, with different mechanisms of interaction dominating at different energies. For example, in the case of lower energy x-rays (i.e. kV range), in addition to the effects of material density, x-ray absorption can be quite material sensitive due to the photoelectric effect. Different materials absorb kV x-rays differently (e.g. as seen in the clear imaging of bone in kV x-rays). However, at higher energy levels (i.e. MV range) the relative absorption depends mainly on the relative material density of the materials in the object. At MV energy levels, therefore, a high contrast image can be obtained by imaging materials with different material densities. The greater the difference in material density, the greater the contrast in the image.

The marker 10 according to embodiments of the present invention can be employed in imaging systems employing these and other techniques.

The marker 10 comprises a first marker component 12 which is solid and, in the illustrated embodiment, has a spherical shape. As will be explained in greater detail below, however, the first marker component 12 may take different shapes in different embodiments of the invention.

The first marker component 12 is non-magnetic, in that it has no significant effect on an external magnetic field (i.e. it is non-ferromagnetic). It is this feature which allows the marker 10 to be employed in magnetic resonance imaging (MRI) systems. Further, in some embodiments of the invention, the first marker component 12 is non-conductive, as conductive materials can cause distortion in MR images. In the context of the present invention, a component can be deemed non-conductive if the radio frequency field generated by an MRI system can penetrate (i.e. pass through) the component. The skin depth of the component material at such frequencies must therefore be substantially equal to or greater than the size of the component itself (the skin depth $\delta$ is given by $$\delta = \sqrt{\frac{2\rho}{\omega\mu}},$$

where $\rho$ is the resistivity, $\omega$ is the angular frequency and $\mu$ is the absolute magnetic permeability). For example, in a 1.5 T MRI the rf field frequency (the resonant frequency of hydrogen protons) will be at or around 64 MHz. Given this information, it is a simple exercise for the skilled person to select a suitable material to ensure that the skin depth is equal to or greater than the size of the component.

The first marker component 12 has a relatively high material density, so that it preferentially absorbs x-rays and appears in radiation-based images, i.e. radiographic images using x-rays. However, the first marker component 12 also has a relatively low hydrogen proton density, so that it appears only weakly in MR images. In some embodiments, the first marker component 12 has substantially zero hydrogen proton density so that it is not imaged in magnetic resonance imaging (MRI) systems.

One class of material which may be suitable for use in the first marker component 12 is ceramic materials, as they are non-magnetic and non-conductive. Certain ceramic materials also have a high material density, such as zirconium oxide (zirconia), which has a material density of 5.66 kgm$^{-3}$.

The marker 10 further comprises a second marker component 14. The second marker component 14 is also non-magnetic (i.e. non-ferromagnetic), but has a relatively low material density (i.e. relative to that of the first marker component 12) and a relatively high hydrogen proton density (again, relative to that of the first marker component 12). In this way, the second marker component 14 is imaged more strongly than the first marker component 12 in magnetic resonance imaging (MRI) techniques, while the first marker component 12 is imaged more strongly than the second marker component 14 in radiographic techniques (i.e. in both MRI and radiographic images, a contrast is achieved between the two components).

In the illustrated embodiment, the second marker component 14 surrounds the first marker component 12, but in other embodiments the second marker component 14 may only be in contact with the first marker component 12 on part of its surface such that, effectively, the two components have at least one common surface. In order that the second marker component 14 can easily conform to the surface of the first marker component 12, the second marker component 14 may be liquid or a malleable solid. According to embodiments of the present invention, the second marker component may also be non-conductive, in that an rf field will penetrate the component as described above. For example, the second marker component 14 may comprise an oil, such as cod liver oil, or an oil-based solid. In alternative embodiments the second marker component 14 may comprise water or a water-based solution.

The marker 10 further comprises a housing 16 which substantially surrounds and supports the other components of the marker 1Q. In one embodiment the housing 16 supports the first marker component 12 at a fixed position within the housing 16. The second marker component 14 substantially fills any voids in the housing 16 not filled by the first marker component 12. The housing 16 may be manufactured from a plastic, such as poly(methyl methacrylate)—otherwise known as Perspex®—and may be transparent or opaque to visible optical light. The housing 16 is non-magnetic. It may also have a substantially zero hydrogen proton density and therefore be substantially invisible to magnetic resonance imaging (MRI) modalities.

In one embodiment, the housing 16 is not rotationally symmetric such that the second marker component 14, which conforms to the shape of the housing 16, is also not rotationally symmetric. In the illustrated embodiment the housing 16 is substantially cylindrical, but those skilled in the art will appreciate that alternative shapes could be employed without departing from the scope of the invention.

The first marker component 12 and/or the housing 16 may take a non rotationally symmetric shape such that their orientation can be determined more accurately when imaged. A spherical object can be easily imaged and measured, but cannot provide information on the orientation of the marker 10. In certain situations that may not matter. However, a non-rotationally symmetric first marker component 12 and/or housing 16 can provide that information.

In further embodiments, the marker 10 may comprise multiple first marker components 12 within the housing 16, each of which can be imaged positively using radiation-based techniques and negatively using MRI-based techniques.

Figure 2A:
FIG. 2a is a schematic illustration of an MR image of the marker of FIG. 1.
Figure 2B:
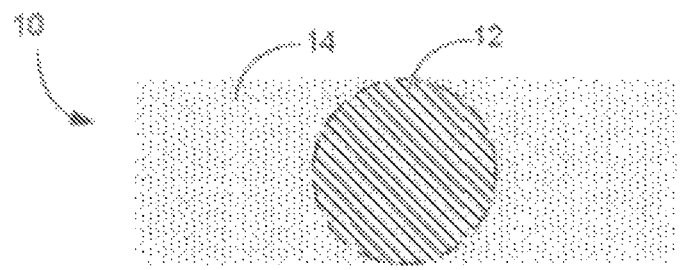
FIG. 2b is a schematic illustration of a radiographic image of the marker of FIG. 1.

FIGS. 2a and 2b are schematic illustrations of MRI-based and radiation-based images respectively of the marker 10 shown in FIG. 1.

In FIG. 2a (MR imaging), the second marker component 14 is visible due to its high hydrogen proton density while the first marker component 12 is less visible (or even invisible) due to the relatively low hydrogen proton density. However, due to the common surface between the two components—shown in FIG. 2a as a dashed line—and the contrast between the two materials in the image, the first marker component 12 can nonetheless be visualized. That is, the spherical space within the second marker component 14 corresponds to the first marker component 12, and therefore the first marker component 12 can be effectively imaged using magnetic resonance imaging (MRI) techniques.

In FIG. 2b (radiography), the first marker component 12 is directly visible as it has a higher material density that the second marker component 14. The second marker component 14 also has a finite material density and therefore also appears in the image. However, due to the difference in material densities, the common surface of the two components (again shown by a dashed line) can be imaged. The centre of the first marker component 12 can therefore act as a common reference point in radiographic and MR images.

Note that the appearance of the first marker component 12 and the second marker component 14 in the radiographic image depends on a number of factors, including the energy of the radiation and the quantity of the radiation (i.e. as determined by the intensity of the beam and the exposure time). A small amount of radiation may result in the second marker component 14 effectively being invisible in the radiographic image. However, it is sufficient that only the first marker component 12 is visible, and that a boundary between the two components can be discerned.

In some embodiments it may desirable to decouple the size of the effective marker as imaged using radiographic techniques from the effective size of the marker 10 as imaged using MRI techniques. For example, a smaller first marker component 12 (i.e. the radiation absorbing component) increases the accuracy of calibration of a radiation based device, whilst use of a relatively large non-magnetic, low density material preserves the accuracy of calibration of a magnetic resonance imaging (MRI) device.

Figure 3:
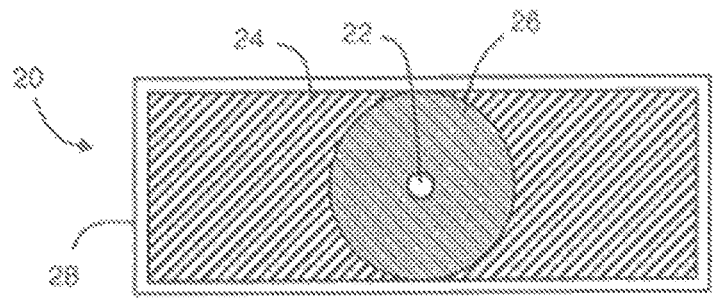
FIG. 3 shows a marker according to embodiments of the present invention.

FIG. 3 shows a cross section of a marker 20 according to embodiments of the present invention. The marker 20 may be employed in an equivalent manner to that of the marker 10 shown in FIG. 1.

The marker 20 comprises a first marker component 22 having equivalent material properties to the first marker component 12 described with reference to FIG. 1, i.e. relatively high material density such that it appears in radiation-based images and relatively low hydrogen proton density so that it appears only weakly in MR images. However, in contrast to the first marker component 12 shown in FIG. 1, the first marker component 22 of FIG. 3 has a relatively small volume such that its position can be ascertained more accurately when imaged using radiation based techniques.

The marker 20 further comprises a second marker component 24. The second marker component 24 is equivalent to the second marker component 14 of the marker 10 described with reference to FIG. 1. In other words, the second marker component 24 is non-magnetic (i.e. non-ferromagnetic), of relatively low material density and has a relatively high hydrogen proton density. Accordingly, the second marker component 24 is imaged more strongly than the first marker component 22 using magnetic resonance imaging (MRI) techniques, while the first marker component 22 is imaged more strongly than the second marker component 24 using radiographic techniques.

It will be appreciated that in the embodiment shown in FIG. 3, no common boundary exists between the first marker component 22 and the second marker component 24. However, in common with the embodiment described with respect to FIG. 1, the coincident centre point of the first marker component 22 and the negative space defined by the second marker component 24 may be used as a common geometric reference point.

The first marker component 22 and the second marker component 24 are separated by an intermediate region 26. In order to hold the first marker component 22 in position relative to the second marker component 24, the intermediate region 26 may be fully or partially manufactured from a non-magnetic, non-metallic material having a relatively low density, such as poly(methyl methacrylate)—otherwise known as Perspex®. It may also have a substantially zero hydrogen proton density and therefore be substantially invisible to magnetic resonance imaging (MRI) modalities. The intermediate region 26 may be completely filled with such a material so as to encapsulate the first marker component 22. Alternatively the intermediate region 26 may comprise a shell and one or more support members manufactured from plastic or similar material, arranged to hold the first marker component 22 in a concentric position relative to the shell such that the first marker component 22 and the void within the second marker component 24 have a common centre. In which case the remainder of the intermediate region 26 may be filled with air or any other material which is substantially invisible to magnetic resonance imaging (MRI) modalities.

The marker 20 further comprises a housing 28 equivalent to the housing 16 shown in FIG. 1 which substantially surrounds and supports the other components of the marker 20. In one embodiment the housing 28 supports the intermediate region 26 at a fixed position within the housing 28. The second marker component 24 substantially fills any voids in the housing 28 not filled by the first marker component 22 or the intermediate region 26. Like the intermediate region 26, the housing 28 may be manufactured from a plastic, such as Perspex® and may be transparent or opaque to visible optical light. It may also have a substantially zero hydrogen proton density and therefore be substantially invisible to magnetic resonance imaging (MRI) modalities.

In further embodiments, the marker 20 may comprise multiple first marker components 22 and multiple corresponding intermediate regions 26 within the housing 28. Each of the first marker components 22 may be imaged positively using radiation-based techniques, while the voids defined by the first marker components 22 and the intermediate regions 26 may be imaged negatively using magnetic resonance imaging (MRI)-based techniques.

Figure 4A:
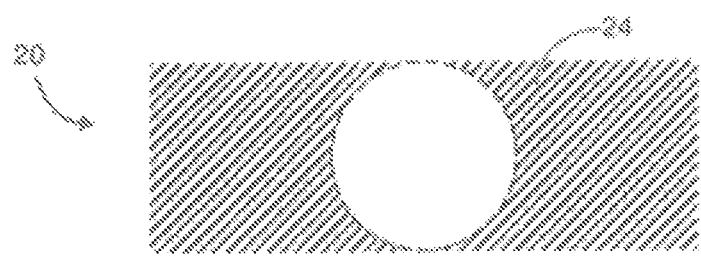
FIG. 4a is a schematic illustration of an MR image of the marker of FIG. 3.
Figure 4B:
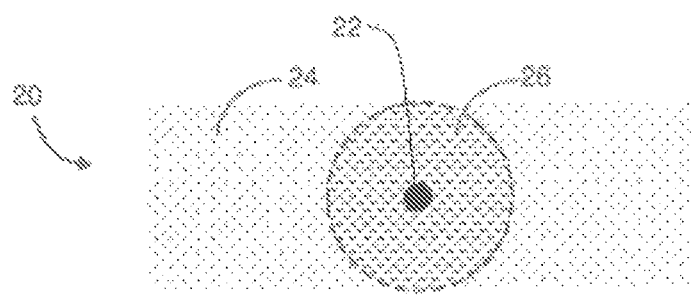
FIG. 4b is a schematic illustration of a radiographic image of the marker of FIG. 3.

FIGS. 4a and 4b are schematic illustrations of magnetic resonance imagine (MRI)-based and radiation-based images respectively of the marker 20 shown in FIG. 3.

In FIG. 4a (magnetic resonance imaging (MRI)), the second marker component 24 is visible due to its high hydrogen proton density while the first marker component 22 and the intermediate region 26 are less visible (or even invisible) due to their relatively low hydrogen proton density. However, the border—shown as a dashed line—between the magnetic resonance imaging (MRI)-imageable second marker component 24 and the intermediate region 26 can be visualized due to their relative hydrogen proton densities.

In FIG. 4b (radiography), the first marker component 22 is directly visible as it has a high material density. The second marker component 24 also has a finite material density and therefore also appears in the image. However, due to its relatively low material density, this component 24 appears faintly. Equally, the intermediate region 26 has a relatively low material density and as such shows up faintly relative to the high density first marker component 22 in the image. Due to the difference in material densities of the first marker component 22 and the intermediate region 26, the common surface between these two components can be imaged.

As with the marker 10 shown in FIG. 1, the appearance of the first marker component 22 and the second marker component 24 and the intermediate region 26 in the radiographic image depends on a number of factors, including the energy of the radiation and the quantity of the radiation (i.e. as determined by the intensity of the beam and the exposure time). A small amount of radiation may result in the second marker component 24 and the intermediate region 26 effectively being invisible in the radiographic image. However, it is sufficient that only the first marker component 22 is visible, and that a boundary between the intermediate region 26 and the first component 22 can be discerned.

The utility of the marker 10 and the marker 20 will now be apparent to those skilled in the art. The same surface can be imaged using magnetic resonance imaging (MRI) and radiographic techniques, and moreover the centre of the first marker component 12, 22 and the centre of the void in the second marker component 14, 24 is the same, allowing the marker 10 and, the marker 20 to be employed in imaging systems using either or both modalities.

It will be apparent to those skilled in the art that in each of the embodiments described above, the first marker component 12, 22 and the second marker component 14, 24 may be swapped with each other without substantially affecting the ability of the marker 10 and the marker 20 to be imaged in radiographic and magnetic resonance imaging (MRI) modalities. For example, the marker may comprise a first (solid) marker component with a cut out for the second marker component.

In further embodiments, the first marker component 12, 22 may have a lower material density than the second marker component 14, 24. As long as there is a difference between the two marker components in hydrogen proton density and material density, a contrast is achieved that allows the marker components to be imaged. It will however be appreciated that for radiation imaging, a relatively small marker component is preferable and for magnetic resonance imaging (MRI), a relatively large marker component is desirable.

As described above, phantoms are known devices which are scanned or imaged to evaluate and tune the performance of various medical imaging devices. In one embodiment, either of the marker 10 and the marker 20 themselves can be employed as a phantom. That is, the dimensions of the marker 10 and of the first marker component 12 may be made sufficiently large that an image of the marker 10 on its own provides sufficient accuracy to enable the imaging system to be calibrated. For example, if the first marker component 12 has a largest dimension in the order of 100 mm, the marker 10 may be placed in the imaging system on its own as part of the calibration process. Equally, if the first marker component 22 of the marker 20 has a largest dimension in the order of 100 mm, for example, the marker 20 may be placed in the imaging system on its own as part of the calibration process. Alternatively, a marker 10 and a marker 20 as described above and comprising multiple first marker components may be used on its own as a phantom.

Figure 5A:
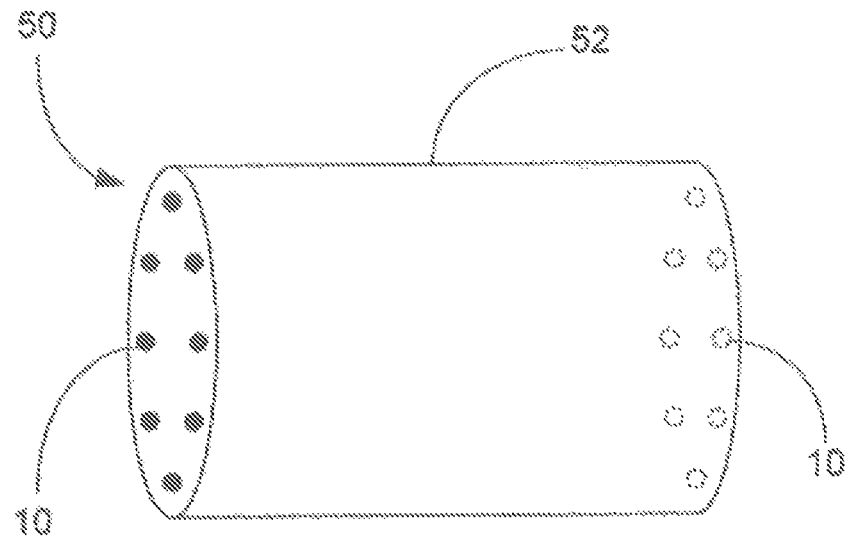
FIG. 5a shows a phantom according to embodiments of the present invention.
Figure 5B:
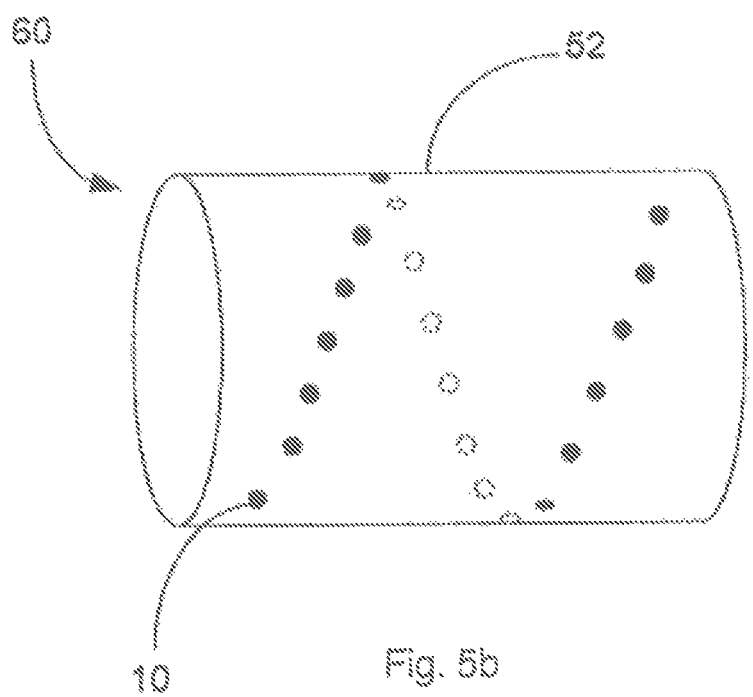
FIG. 5b shows a phantom according to further embodiments of the present invention.

However, sourcing and producing such a large device may be impractical due to issues of cost and efficiency. In other embodiments of the invention, either of the marker 10 and the marker 20 may be produced on a smaller scale such that the first marker components 12, 22 have a largest dimension in the order of 10 mm. In this way, conventional phantoms can be adapted to include a plurality of such markers arranged in one or more patterns. FIGS. 5a and 5b show examples of such phantoms.

FIG. 5a shows a phantom 50. The phantom 50 has a housing 52 which may be manufactured from a non-magnetic, non-conductive material such as plastic. In the illustrated embodiment the housing 52 is cylindrical but in practice any shape may be employed. The housing 52 has a number of attaching points (not illustrated), to which the markers 10 shown in FIG. 1 and/or the markers 20 shown in FIG. 3 are attached. Any means of attaching the markers 10 to the housing 52 can be used. For example, slots or openings may be provided in the housing 52, into which the markers 10 can be inserted. In this example, the markers 10 are arranged in two circles, one at each end of the cylindrical housing 52.

FIG. 5b shows a further example of a phantom 60 according to embodiments of the invention. In this example, the markers 10 are arranged in a helical pattern around the housing 52.

In either case, the pattern of markers 10 allows the phantom's location and orientation to be precisely measured.

Whilst the phantom 50 shown in FIG. 5a comprises markers 10 of the type shown in FIG. 1 only, it will be appreciated that the housing 52 may additionally or alternatively include markers 20 of the type shown in FIG. 3. The choice of which marker to use may depend on the particular device being calibrated or the accuracy of calibration required, amongst other factors.

Figure 6:
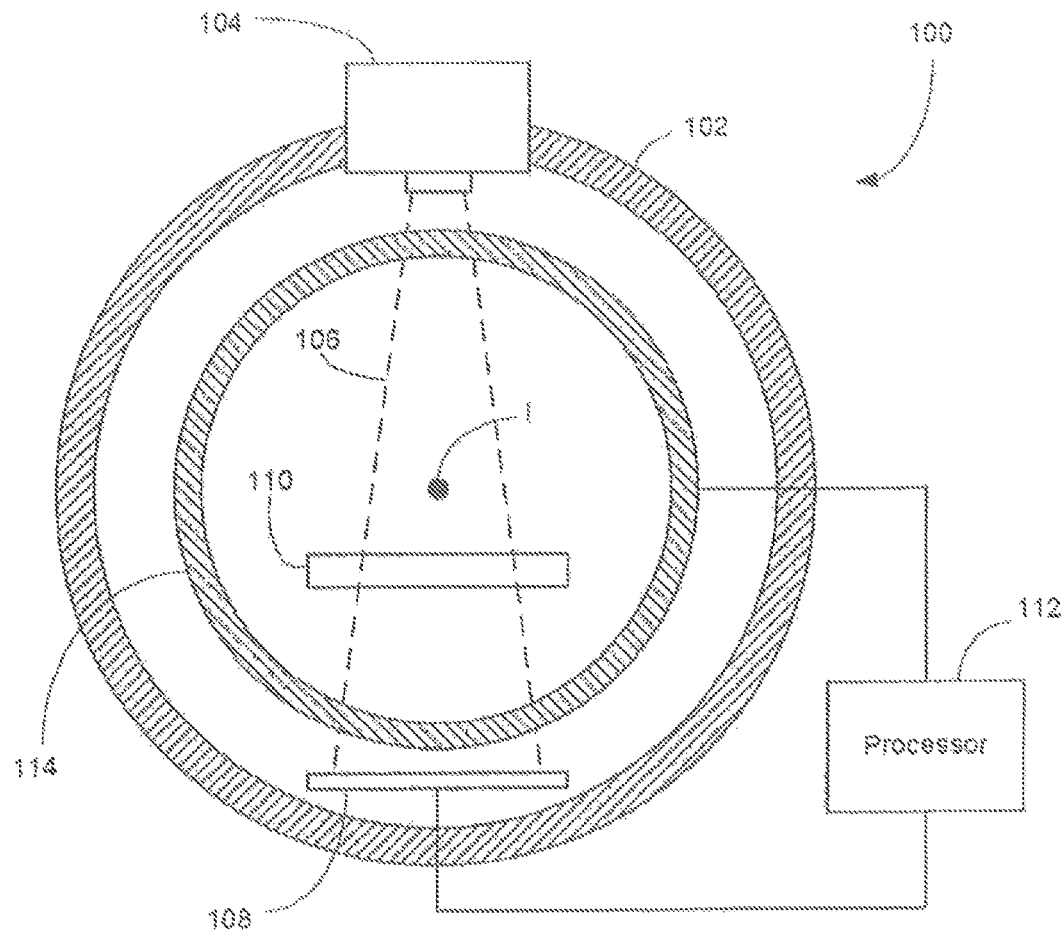
FIG. 6 shows a combined MRI radiotherapy system.

It will be apparent from the description above that markers and phantoms according to embodiments of the present invention can be employed in imaging systems using a variety of imaging modalities, such as radiography and magnetic resonance. The markers and phantoms also have particular utility within MRI-Linac systems, which combine both magnetic resonance imaging (MRI and radiotherapy within the same system. Such an MR-Linac system 100 is shown schematically in FIG. 6.

The MRI-Linac system 100 comprises a gantry 102, which is able to rotate about an axis I. A radiation head 104 is mounted to the gantry 102, and adapted to generate a beam of radiation 106 directed substantially inwards towards the rotation axis I. A source of radiation (such as a linear accelerator, or a radioisotope) may be provided to generate the radiation which emanates from the radiation head 106. In order to have a therapeutic effect, the energy of the radiation beam 106 will typically be in the order of megaelectronvolts. A patient support 110 is provided on or near the rotation axis I, on which a patient or an object to be imaged can be placed.

The shape and direction of the radiation beam 106 can be adapted by the use of collimators such as a multi-leaf collimator (not illustrated), to conform to a particular desired profile. For example, the shape of the radiation beam 106 may be adapted to conform to the profile of a target structure within a patient on the patient support 110. As the gantry 102 rotates, the radiation beam 106 is directed towards the target structure from multiple directions and dose builds up in the target structure while being generally reduced in the surrounding areas.

A radiation detector 108 is mounted on the gantry 102 at a position substantially opposite the radiation head 104, such that the radiation beam 106 impacts the radiation detector 108 after passing through an object to be imaged on the patient support 110. Such detectors are often called portal imagers as they generate a projection image of the object along the axis of the radiation beam 106. The radiation detector 108 is coupled to processing circuitry 112 which uses the detection data to produce an image. Thus, although the MRI-Linac system 100 is primarily used for therapeutic purposes and generates radiation beam 106 at an energy suitable for therapy, the radiation can nonetheless be used to generate images (albeit at lower contrast than the less energetic radiation conventionally used for imaging).

The MR-Linac system 100 further comprises a magnetic resonance imaging apparatus. Those skilled in the art will appreciate that such an apparatus comprises a large number of components, including various magnetic coils 114 for generating specific magnetic field strengths at specific locations and an RF system for transmitting and receiving electromagnetic waves. Only the magnetic coils 114 are illustrated here for clarity.

The magnetic coils 114 are positioned with their longitudinal axes aligned with the rotational axis I of the gantry 102. In one embodiment, the magnetic coils 114 are displaced from each other along the direction of the axis I such that a gap is created. The radiation beam 106 can be directed through this gap such that the magnetic coils 114 do not interfere with the radiation beam 106. The magnetic coils 114 are coupled to the processing circuitry 112 such that an image can be produced of an object on the patient support 110.

An object which is placed on the patient support 110 can therefore be imaged by the MRI system and treated by the radiotherapy system while in the same position. Further, the radiotherapy system can be used to generate a portal image of the object using the radiation detector 108. The markers 10, 20 and phantoms 50, 60 described above can be used to calibrate the MRI-Linac system 100 such that imaging data collected by the MRI system can be used to inform and control the radiotherapy system.

Figure 7:
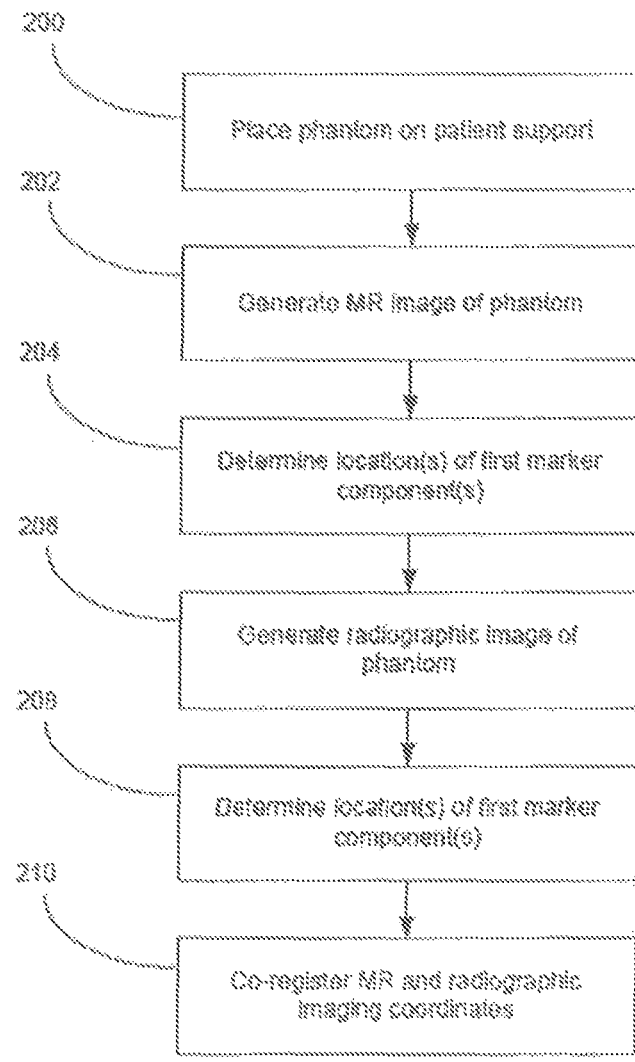
FIG. 7 is a flowchart of a method according to embodiments of the present invention.

FIG. 7 is a flowchart describing a method of calibrating the MRI-Linac system 100 described above.

In step 200, a phantom according to embodiments of the invention is placed on the patient support 110, in the path of the radiation beam 106 and at a position suitable for imaging by the MRI system. The phantom may be a single marker 10, 20 as shown in FIG. 1 or FIG. 3, or a plurality of such markers as shown in FIGS. 5a and 5b.

In step 202, the MRI system is used to generate an image of the phantom, and particularly used to generate an image showing the locations of the one or more second marker components. In this way, the first marker component can also be imaged because of the common boundary between the two component types.

In step 204, the locations of the one or more first marker components are determined from the MRI image.

In step 206, a radiographic image is generated of the phantom using the radiation beam 106 and the radiation detector 108 while in the same position. In this image, the one or more first marker components show more clearly due to their higher material density.

In step 208, the locations of the one or more first marker components are determined from the radiographic image.

In step 210, the knowledge of the first marker component locations in both images allows the coordinate systems of the magnetic resonance imaging (MRI) modality to be co-registered with the coordinate system of the radiographic modality. In particular, measurements using the MRI system can be used to instruct the radiotherapeutic system. For example, the positions of the collimating elements may be adapted on the basis of magnetic resonance imaging (MRI) data in order to track a moving target.

Embodiments of the present invention therefore provide markers, phantoms, and associated methods of calibration which are suitable for use in a wide variety of medical imaging systems.

Those skilled in the art will appreciate that various amendments and alterations can be made to the embodiments described above without departing from the scope of the invention as defined in the claims appended hereto.

The invention claimed is:

1. A marker for use in calibration of a medical imaging system, comprising:
    a first component having a first hydrogen proton density and a first mass density, the first component being configured to absorb x-rays in a radiation-based imaging modality;
    a second component having a second hydrogen proton density greater than the first hydrogen proton density, the second component able to be imaged in a magnetic resonance imaging modality, the second component further having a second mass density lower than the first mass density such that the second component is imaged less strongly than the first component in the radiation-based imaging modality; and
    a common intermediate region made of a material which is not able to be imaged using the magnetic resonance imaging modality, wherein:
        a surface of the first component and a surface of the second component abut the common intermediate region;
        the first component, the second component, and the common intermediate region are non-magnetic; and
        the second component comprises a void, the first component being positioned concentrically within the void.

2. The marker according to claim 1, wherein the common intermediate region has a third hydrogen proton density different than the second hydrogen proton density, and a third mass density different than the first mass density.

3. The marker according to claim 1, wherein the first component and the second component are such that a contrast is formed between the first component and the second component in the radiation-based imaging modality, and an opposite contrast is formed between the first component and the second component in the magnetic resonance imaging modality.

4. The marker according to claim 1, wherein the first component comprises a ceramic material.

5. The marker according to claim 1, wherein the first component has a substantially zero hydrogen proton density.

6. The marker according to claim 1, wherein the second component is a liquid.

7. The marker according to claim 6, wherein the first component is at least partially submerged within the second component.

8. The marker according to claim 1, wherein the first component comprises a spherical object.

9. The marker according to claim 1, wherein the first component comprises a rotationally asymmetric object.

10. The marker according to claim 1, further comprising a housing in which the first component and the second component are arranged.

11. The marker according to claim 10, wherein the housing is rotationally asymmetric.

12. The marker according to claim 1, wherein the first hydrogen proton density is lower than the second hydrogen proton density, and wherein the first material density is greater than the second material density.

13. A phantom for use in one or more medical imaging systems, comprising:
one or more markers according to claim 1.

14. The phantom according to claim 13, wherein the one or more markers comprise a plurality of markers according to claim 1.

15. The phantom according to claim 14, wherein the phantom comprises a housing having a plurality of attaching points to which the plurality of markers can be attached.

16. A method of calibrating an imaging apparatus, the method comprising:
placing a phantom according to claim 13 in an imaging volume;
generating an image of the phantom with the imaging apparatus; and
determining locations of at least one of the first component and the second components in the image.

17. The method of claim 16, wherein the imaging apparatus is integrated with a radiotherapy apparatus, the radiotherapy apparatus comprising a source of radiation generating a radiation beam passing through a treatment volume and a radiation detector for detecting the radiation beam after it has passed through the treatment volume, and wherein the treatment volume is coincident with the imaging volume, the method further comprising:
generating a radiation beam passing through the treatment volume and forming a second image of the phantom with the radiation detector;
determining locations of at least one of the first component and the second component in the second image; and
co-registering coordinate systems of the radiotherapy apparatus and the imaging apparatus.

* * * * *